United States Patent [19]

Apple et al.

[11] Patent Number: 4,726,366
[45] Date of Patent: Feb. 23, 1988

[54] APPARATUS AND METHOD FOR CONTROLLING LUNG VENTILATION

[75] Inventors: Wayne R. Apple; James A. Hoerlein, both of Boulder; G. Kenneth Russell, Castle Rock, all of Colo.

[73] Assignee: Life Products, Incorporated, Boulder, Colo.

[21] Appl. No.: 853,574

[22] Filed: Apr. 18, 1986

[51] Int. Cl.[4] .............................................. A61M 16/00
[52] U.S. Cl. ............................ 128/204.21; 128/205.18
[58] Field of Search ...................... 128/205.18, 204.21, 128/204.22, 204.23, 205.13, 205.14, 205.15; 417/45; 318/661

[56] References Cited

U.S. PATENT DOCUMENTS

| | | | |
|---|---|---|---|
| 3,358,681 | 12/1967 | Chabanier | 128/205.18 |
| 4,036,221 | 7/1977 | Hillsman et al. | 128/204.23 |
| 4,141,355 | 2/1979 | Apple | |
| 4,243,029 | 1/1981 | Apple | 128/204.21 |
| 4,262,667 | 4/1981 | Grant | 128/205.14 |
| 4,490,661 | 12/1984 | Brown et al. | 318/661 |
| 4,587,967 | 5/1986 | Chu et al. | 128/205.18 |

FOREIGN PATENT DOCUMENTS

| | | | |
|---|---|---|---|
| 2822030 | 7/1978 | Fed. Rep. of Germany | 128/205.18 |
| 1541852 | 3/1979 | United Kingdom | 128/204.21 |

*Primary Examiner*—Edward M. Coven
*Assistant Examiner*—J. P. Lacyk
*Attorney, Agent, or Firm*—Sheridan, Ross & McIntosh

[57] ABSTRACT

A lung ventilator is provided that reduces the number of mechanical components and is able to rapidly adjust to provide a selected volume of air or other gas for delivery to a patient's lungs. The ventilator includes a brushless-type DC electric motor having a number of coils that are energized in a predetermined manner to cause reciprocating movement of a piston within a cylinder. The retracted end position of the piston in a cylinder is used to define the volume of air that is to be received by the patient. Three Hall sensors are connected to the motor at predetermined locations and sense the position of the rotor as it rotates due to the energization of the coils. Each of the pulsed outputs from the Hall sensors is out-of-phase relative to the other Hall sensor outputs. The six different binary outputs of the Hall sensors are identified so that a ROM is able to provide a predetermined output for each of the identified Hall sensor combinations inputted to the ROM. The outputs from the ROM are applied to driving transistors, the outputs of which are applied to the motor coils to cause desired rotational movements of the motor rotor. The position of the piston is monitored also using the Hall sensor outputs. The actual position of the piston is found and compared with the desired or selected position of the piston, which is based on a selected volume of gas to be sent to the patient. When the actual position of the piston corresponds to the selected position, piston movement is stopped. A reference sensor is used in determining a reference piston position from which the actual piston position can be found at any instance in time. The present invention also includes a one-piece manifold to which the cylinder is mounted. The manifold includes a number of passageways along which air is carried to the patient.

11 Claims, 9 Drawing Figures

Microfiche Appendix Included
(2 Microfiche, 136 Pages)

APPARATUS AND METHOD FOR CONTROLLING LUNG VENTILATION

A Microfiche Appendix is included in this application and consists of 2 microfiche having 136 frames.

FIELD OF THE INVENTION

The present invention relates to a respiratory apparatus and, in particular, to method and apparatus for controlling the volume of air, or other gas, delivered to a patient's lungs.

BACKGROUND INFORMATION

Numerous techniques have been developed or advanced for controlling the volume of air or other gas to be delivered to a patient suffering from one or more respiratory deficiencies. Particularly in conjunction with portable ventilators, it is known to utilize complicated ratchet and gear mechanisms together with a brush-type electric motor for controlling the movement of a piston. The retracted position of the piston, at one end of its cycle, defines the volume of air to be provided to the user of the ventilating machine. It is common practice for the operator to be able to adjust the volume of air or gas to be delivered to a patient using such machines. Such adjustment is important so that individualized respiratory treatment is available, i.e. the volume of air and the velocity of piston movement can be controlled to achieve a desired inspiration/expiration cycle for each patient. In U.S. Pat. No. 4,141,355 to Apple, issued Feb. 27, 1979 and entitled "Apparatus For Automatic Ventilation of the Lungs", a mechanism is disclosed for changing the volume of air that can be delivered and is characterized by the use of a ratchet wheel, a sliding block, and a jack screw. These members cooperate to effect movement of a piston in order to change the volume of air that is being provided to a patient.

Although prior art devices may work satisfactorily, there remains a need for a ventilator that reduces the number of mechanical components used to control the amount of gas for ventilating a patient and thereby achieve lower mechanical inertia in the total respiratory system.

SUMMARY OF THE INVENTION

In connection with achieving such objectives, a ventilator apparatus is provided for controlling the volume of air to be delivered to a patient. The apparatus includes a motor assembly comprising a brushless-type DC electric motor, preferably having three inter-connected coils or windings. The motor is powered or driven using a motor driver circuit, which includes a number of transistors. Each of the inputs to the transistors is electrically connected to a Read-Only-Memory (ROM). Depending upon which inputs of a number of known inputs is currently being inputted to the ROM, the ROM is programmed to power selected transistors for energizing the motor coils in a predetermined manner in order to effect the desired rotational movement of the rotor. In addition to the rotor, the brushless-type motor includes a stator to which a number of Hall or magnetic sensors are fastened. Each of these magnetic sensors detects the presence of rotor poles that pass the sensors. In the preferred embodiment, three magnetic sensors are located in predetermined positions such that each of their outputs is out-of-phase relative to the other sensor outputs and the motor rotor contains an 8-pole permanent magnet. In this embodiment, each of the three sensors provides a pulsed output such that there are a total of 24 changes of state or codes per revolution of the rotor. The outputs of the magnetic sensors are applied to the ROM. Signals are also inputted to the ROM from a microprocessor in order to control the rotational direction and energization of the motor. A speed control signal is also applied to the ROM from comparator circuitry to cause the motor to rotate at the desired speed.

The apparatus further includes a gear box assembly, which is operatively connected to the rotor. The gear box assembly provides a higher degree of resolution for positioning the piston whereby the selected volume of air to be delivered to a patient is more precisely controlled. The output gear of the gear box assembly operatively engages a crank arm assembly that is connected to a piston for use in causing reciprocating movement of the piston within a cylinder. In conjunction with controlling the position of the piston, a reference magnetic sensor is located adjacent to the gear box and crank arm assemblies. In the preferred embodiment, the reference sensor provides an indication to the microprocessor that the piston is positioned at a known location near its bottom dead center position. The microprocessor counts codes received from the Hall sensors, which are used to determine the current location of the piston. In the preferred embodiment, the predetermined or selected volume of air is inputted by the user or the operator using an operating panel that communicates with the microprocessor. Based on this input relating to the desired volume, the microprocessor is programmed to determine the number of Hall sensor codes from bottom dead center that equate to the selected volume. Consequently, when the number of Hall sensor codes that are counted from the bottom dead center position equals the predetermined count, based on the selected volume, the microprocessor causes movement of the piston to stop so that it completes its stroke at the desired position in the cylinder. This reciprocating movement of the piston is continued at a desired rate until a new or different volume of air is selected by the operator.

The apparatus of the present invention also includes a one-piece or integral manifold to which the cylinder is mounted. The integral manifold has an input assembly to which the air, or other gas, supply is connected. An output assembly is provided on a side opposite that of the input side. The output assembly is used in supplying the desired gas to the patient during the patient's inspiration. The integral manifold is further characterized by the inclusion of passageways for properly receiving gas, as well as providing for the patient's safety, for example, in the case in which the pressure of the delivered gas is greater than a predetermined level.

Based on the foregoing summary, a number of benefits of the present invention are readily discern. The volume control of the present invention significantly reduces the use of relatively complex ratchet and gear mechanisms that have been previously used in ventilators for regulating the volume of air to be delivered to a patient. This reduction in mechanical components results in lower total system mechanical inertia. In addition, the response to the volume adjustment by the operator is accomplished more rapidly so that the desired end position of the piston is more readily achieved. Because of the brushless-type DC motor that is employed, there are no worn out brushes to be replaced.

Relatedly, the motor is energized to cause the rotor to move in clockwise and counter-clockwise directions. As a result, the crank arm assembly rotates only as much as necessary and there is less movement of mechanical parts thereby reducing wear, in comparison with respiratory systems in which the rotor rotates in only one direction, which requires a full rotation for each breath. The use of magnetic sensors, rather than shaft encoders or optical sensors, avoids problems associated with dirt or dust contamination. Finally, a higher resolution of piston position is achieved through the use of the Hall sensors and the gear box assembly.

Additional advantages of the present invention will become readily apparent from the following discussion, when taken in conjunction with the accompanying drawings.

DETAILED DESCRIPTION

Figure 1:
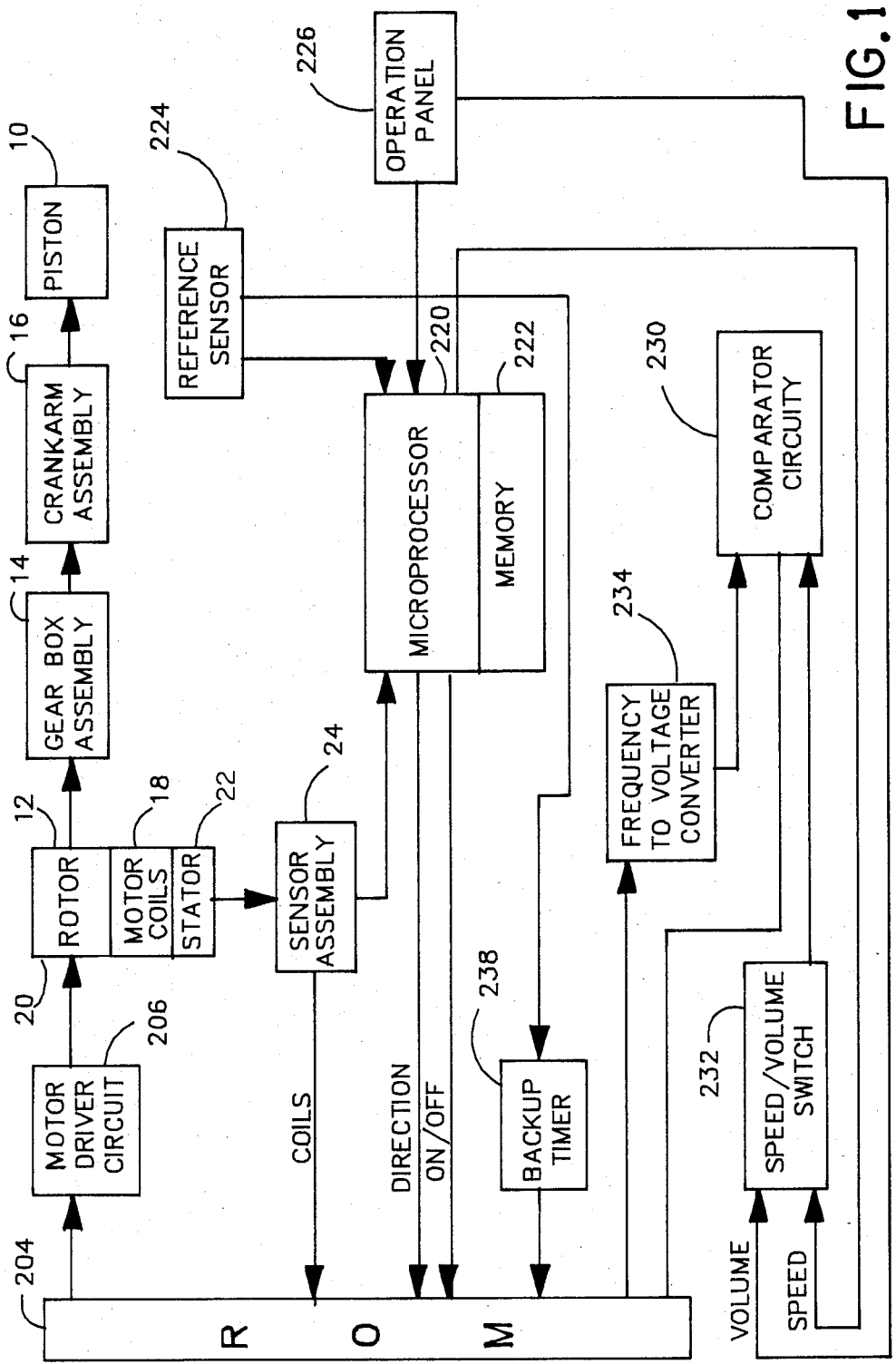
FIG. 1 is a block diagram of the present invention.
Figure 2A:
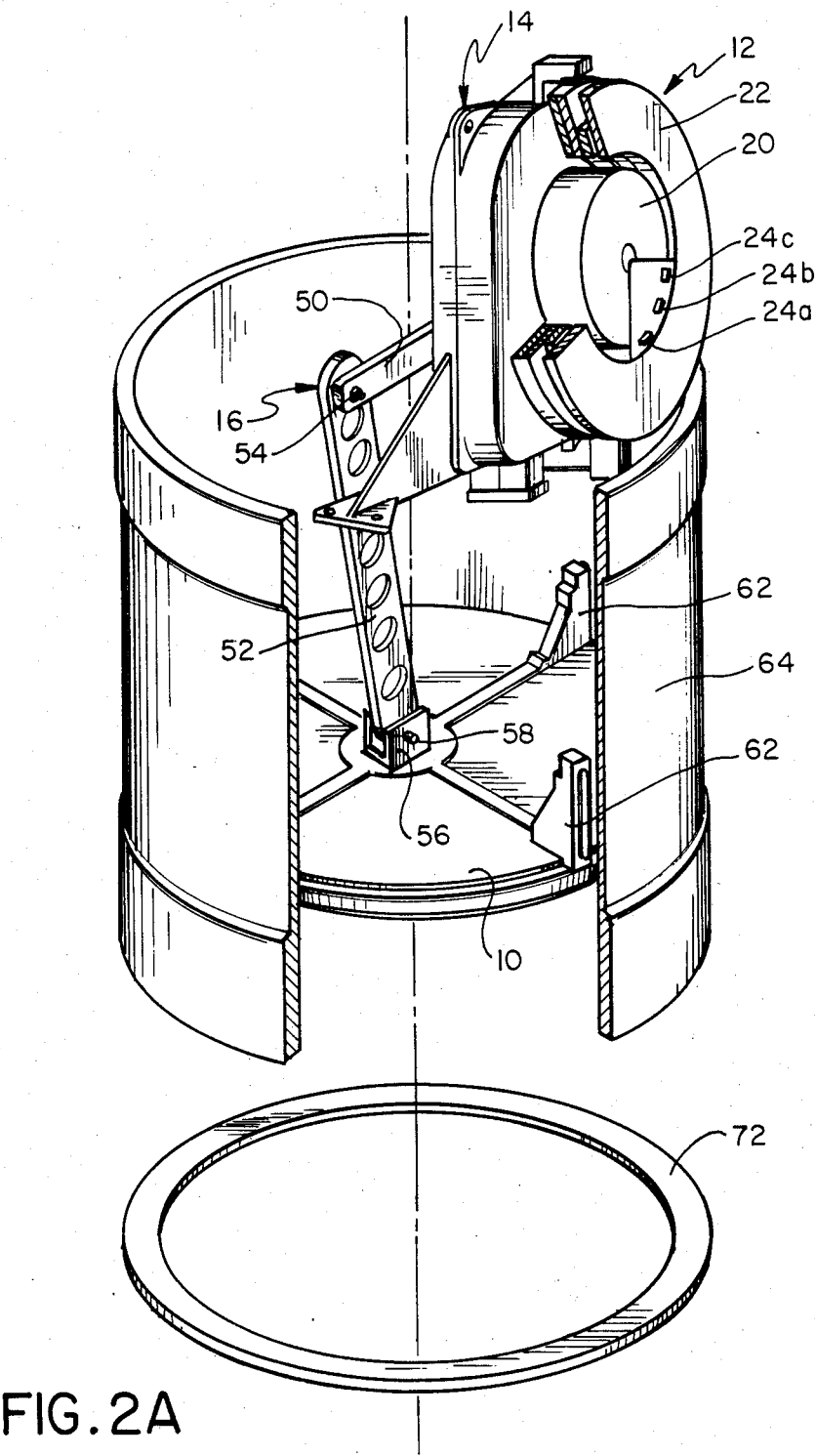
FIGS. 2A-2B illustrate the motor assembly and crank arm assembly of the present invention.
Figure 2B:
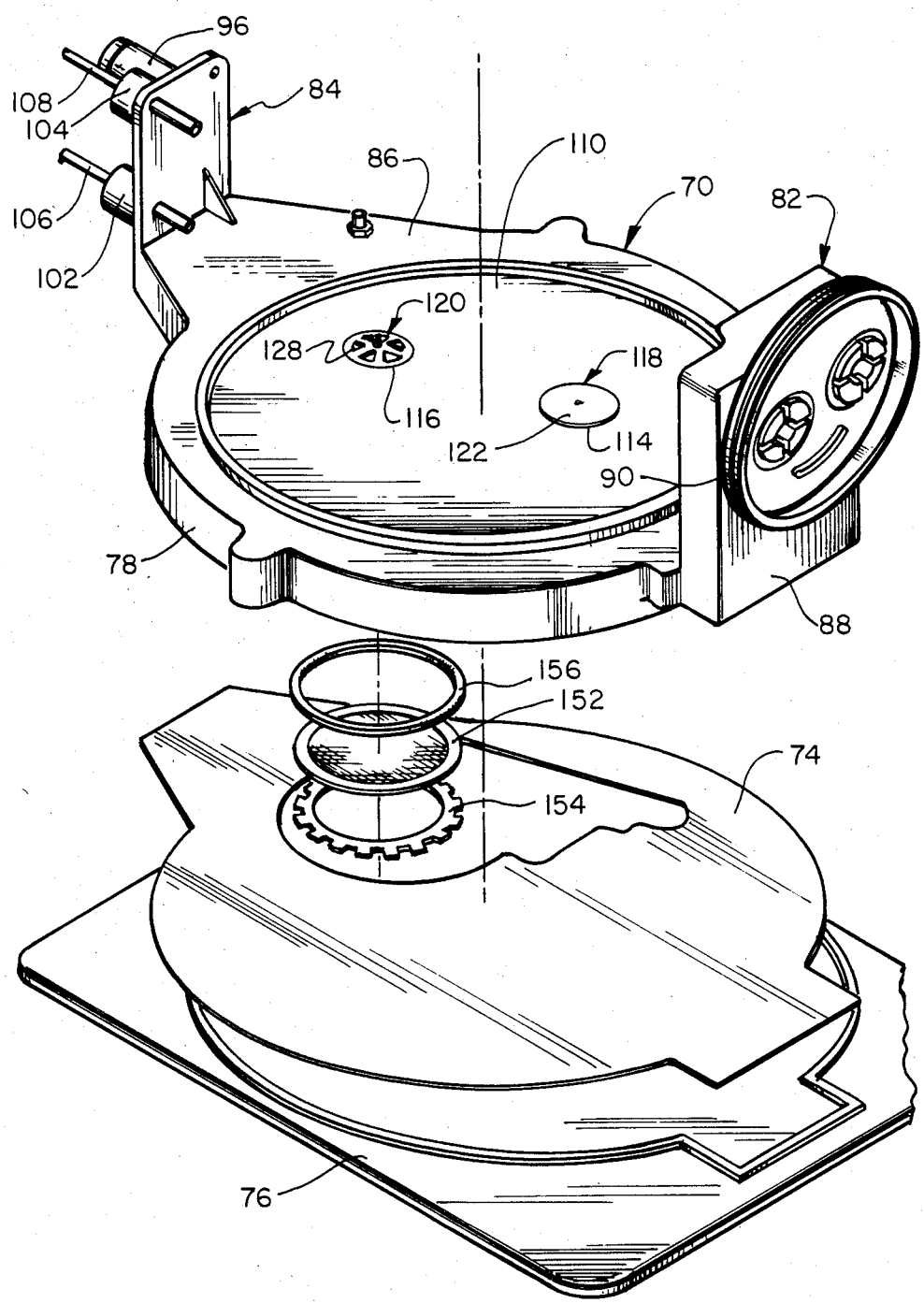

With reference initially to FIGS. 1 and 2A-2B, a respiratory apparatus is illustrated that includes the capability of controlling the volume of gas to be delivered to a patient. Adjustment of the volume of gas is achieved by regulating the stroke of a piston 10. The piston 10 is moved by means of a motor assembly 12, a gear box assembly 14, and a crank arm assembly 16.

Figure 3:
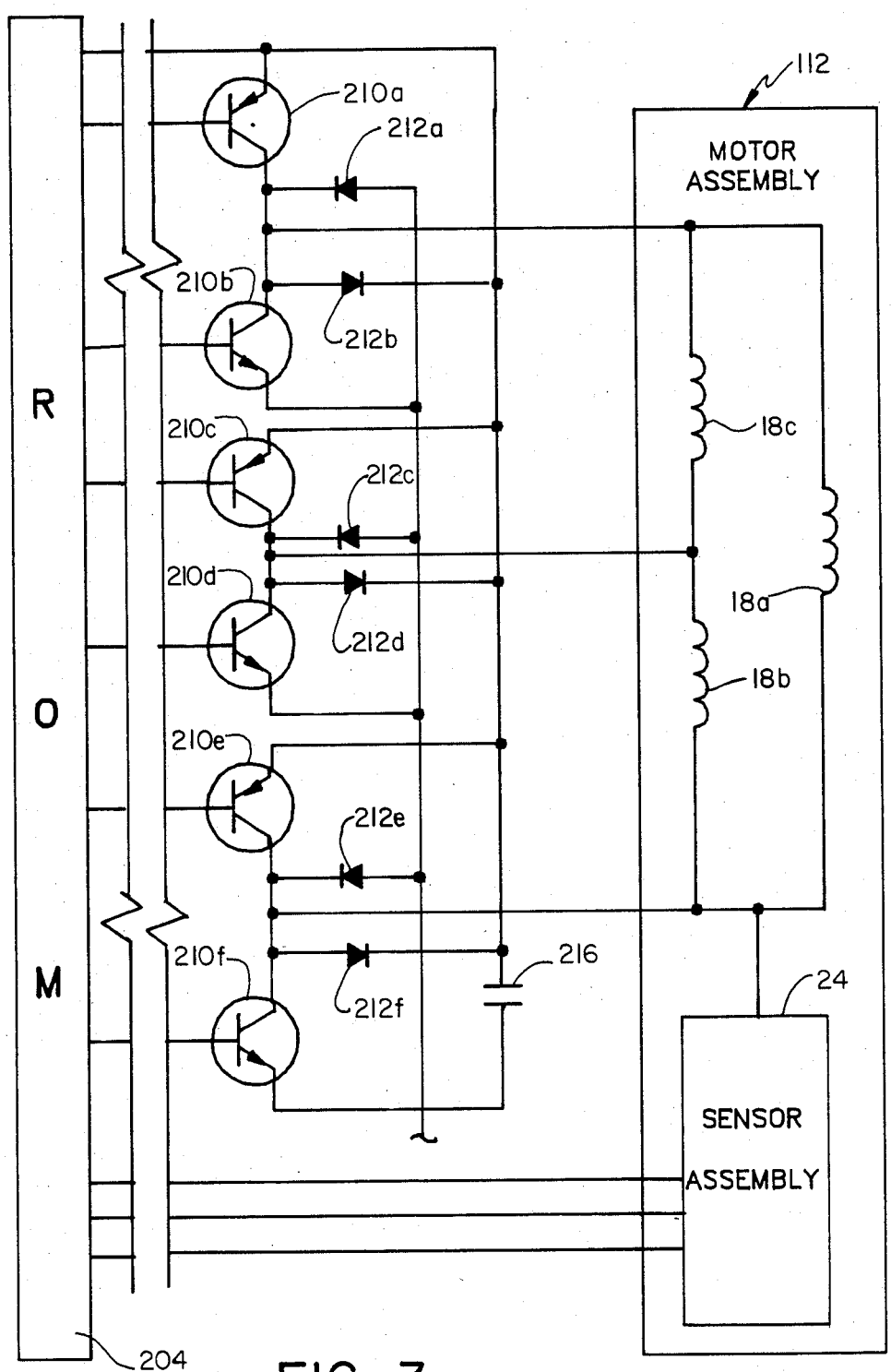
FIG. 3 is a circuit diagram showing further details of the motor coils and motor driver circuit.

The motor assembly 12 is a brushless-type DC electric motor that includes coils 18, a rotor 20 and a stator 22. The motor 12 preferably has, as part of the stator 22, three coils 18a, 18b, 18c. The coils 18a-18c are schematically depicted in FIG. 3. In one embodiment, the rotor contains an 8-pole permanent magnet such that, as the rotor 20 rotates, the positions of the poles can be detected by a sensor assembly 24. The detection of the poles, as will be explained subsequently, is used in controlling both the speed of the motor 12 and the position of the piston 10. The rotor 20 includes a bore formed through the center thereof in order to receive an input shaft 26 for use in coupling the rotary motion of the rotor 20 to the gear box assembly 14. The stator 22 of the motor assembly 12 is concentric with the rotor 20.

Figure 4:
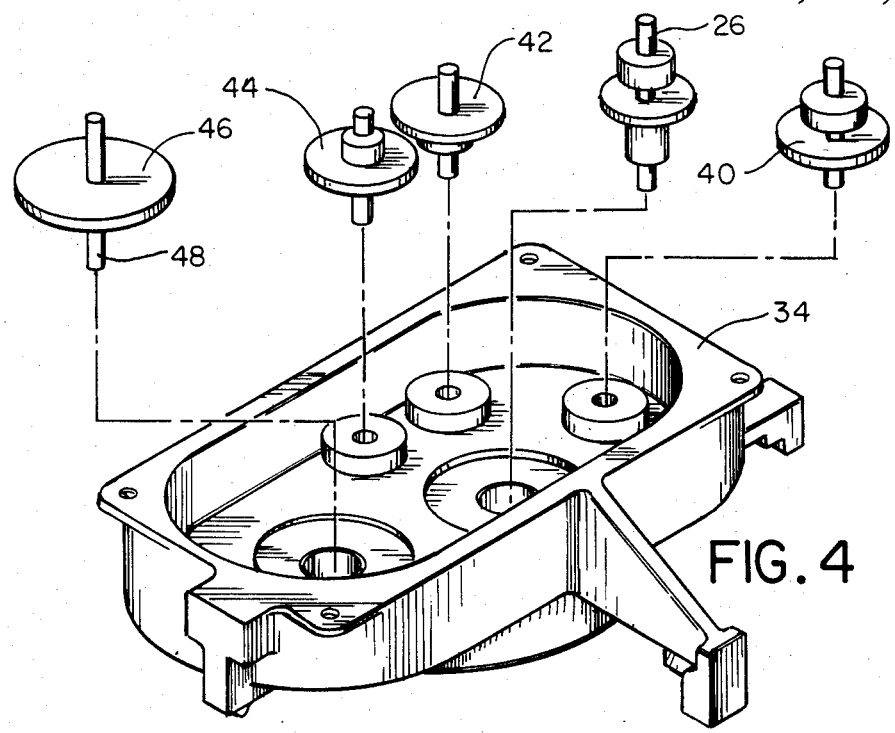
FIG. 4 illustrates further details of the gear box assembly.

The rotational movement of the rotor 20 is coupled to the gear box assembly 14, which is illustrated in greater detail in FIG. 4, using the input shaft 26. The gear box assembly 14 includes a gear box base 34. The rotational movement of the input shaft 26 is coupled to a number of gear stages 40, 42, 44. The rotational movement of the gear stage 44 is coupled to an output gear 46 having an output shaft 48. The output shaft 48 is linked to a fixed radius crank arm 50 of the crank arm assembly 16, as seen in FIG. 2A. The motor stator 20 is fastened to the gear box assembly 14 by conventional means, such as screws.

In addition to the fixed radius crank arm 50, the crank arm assembly 16 also includes a connecting rod 52, which is attached to the crank arm 50 by a pivot pin 54. The opposite end of the crank arm 52 is connected to a U-shaped bracket 56 by means of a pivot pin 58. The bracket 56 is joined to the piston 10. The crank arm assembly 16 configuration enables the piston 10 to reciprocate in response to rotational movements of the output shaft 48 of the gear box assembly 14. Because the output shaft 48 is able to selectively rotate in a clockwise direction or counter-clockwise direction, depending upon the energization of motor coils 18a-18c, the crank arm 52 is able to move in a pendulum-like manner.

As depicted in FIG. 2A, the piston 10 is a disc-shaped member with a number of guide members 62 connected to the same surface of the piston 10 as is the bracket 56. Each of the guide members 62 extends away from the piston surface. The piston 10 and the guide members 62 are contained within a cylinder 64 wherein the guide members 62 act to guide the piston 10 during its reciprocating movement within the cylinder 64. The cylinder 64 also acts to support the gear box assembly 14 as it is mounted at an end surface of the cylinder 64.

The end surface of the cylinder 64, opposite that to which the motor 12 and gear box assembly 14 are attached, is connected to a one-piece or integral manifold 70. A cylinder gasket 72 is positioned between the end surface of the cylinder 64 and the manifold 70 to provide the necessary sealing between the cylinder 64 and the manifold 70. A manifold gasket 74 and an end plate 76 are fastened to the manifold 70 whereby the cooperation of these elements forms passageways in a lower surface 78 of the manifold 70.

Figure 5:
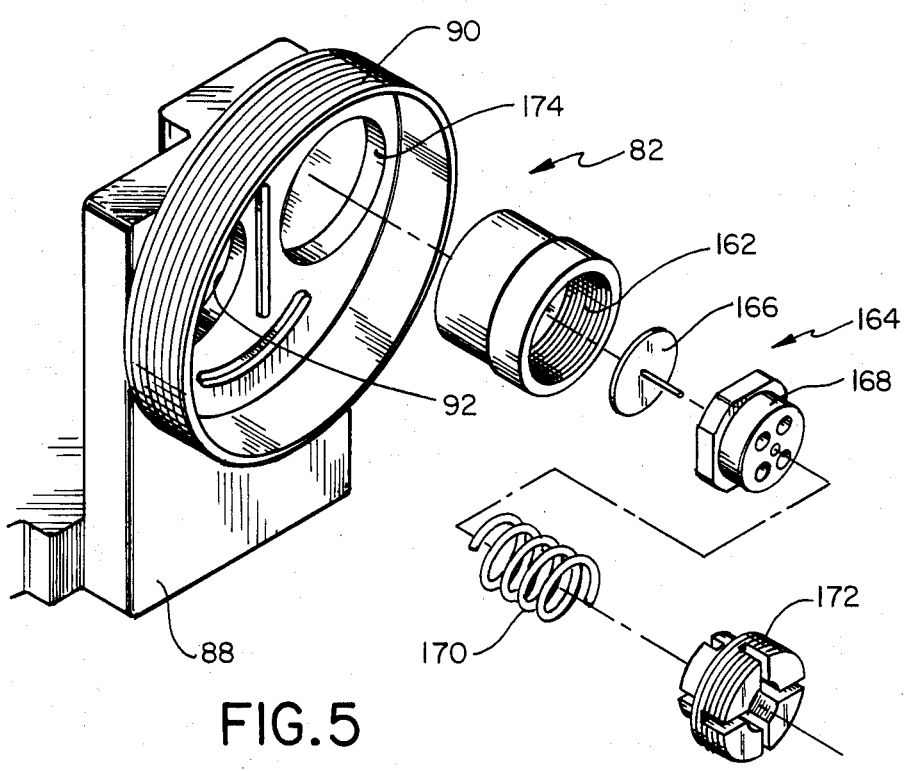
FIG. 5 illustrates the input assembly of the one-piece manifold.
Figure 6:
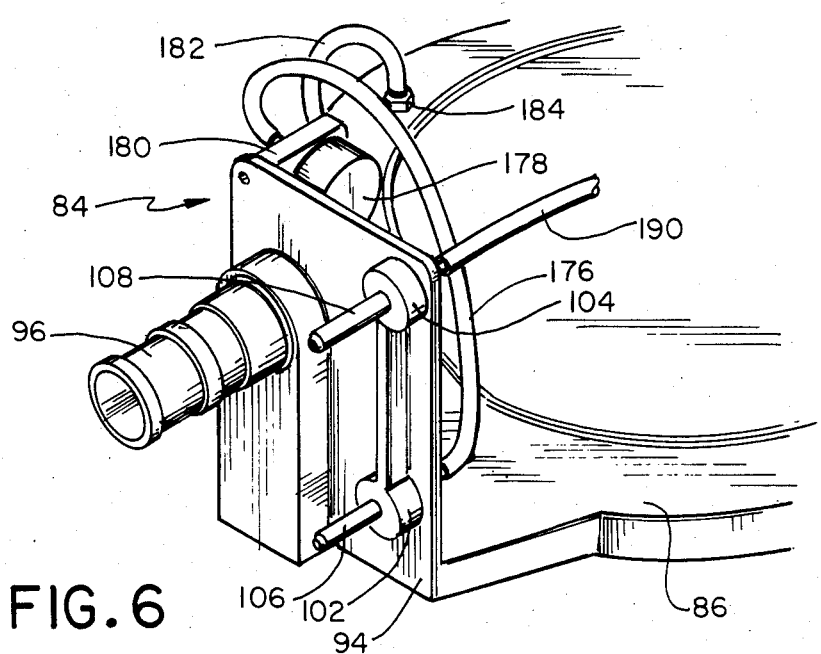
FIG. 6 illustrates the output assembly of the one-piece manifold.
Figure 7:
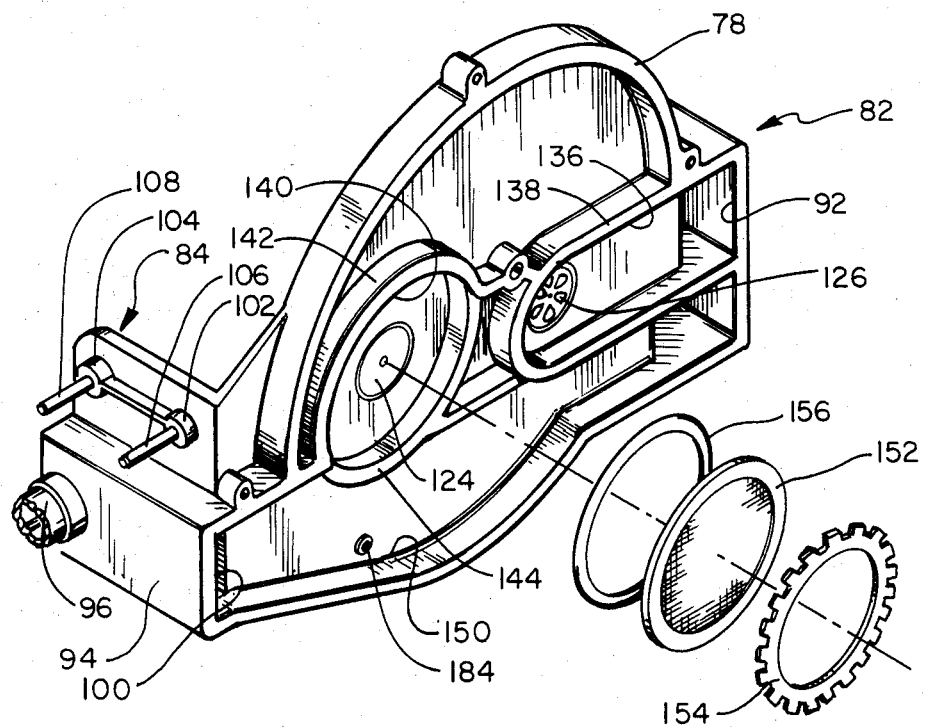
FIG. 7 illustrates a bottom perspective view of the manifold.

Referring now also to FIGS. 5-7, the manifold 70 is described in greater detail. As can be seen, the manifold 70 includes an inlet assembly 82 and an outlet assembly 84. The assemblies 82, 84 are molded as a one-piece unit, with a base member 86 providing the integral connection.

The inlet assembly 82 includes a leg 88 that extends generally perpendicular from the base member 86. Inlet threads 90 are formed at a top portion of leg 88 for holding an inlet filter that delivers air or other gas to the inlet assembly 82. An inlet passageway 92 is formed in leg 88 and extends towards the lower surface 78 of the manifold 70. The outlet assembly 84 includes a leg 94 that is formed integrally with the base member 86 and extends generally perpendicularly therefrom. An outlet passageway 100 is formed through the leg 94 towards the lower surface 78 of the base member 86. The leg 94 also includes an exhalation stem 102 and a pressure stem 104, which are formed integrally with the leg 94. The exhalation stem 102 includes a hole for receiving a peice of metal tubing 106 that is separate from the exhalation stem 102. Similarly, the pressure stem 104 has a hole for receiving a metal piece of tubing 108, which is separate from the pressure stem 104.

The base member 86 of the manifold 70 has an inner surface 110 on which the cylinder gasket 72 and cylinder 64 are supported. The inner surface 110 also has a pair of holes 114, 116 formed therein. An inlet check valve 118 is held in the hole 114 while an outlet check valve 120 is held in the hole 116. Each of the two valves 118, 120 includes a leaf 122, 124 and a spoked wheel 126, 128, respectively. Each of the spoked wheels 126, 128 includes a beveled portion which faces towards the direction of desired air flow.

With respect to the lower surface 78 of the base member 86, a passageway 136 is formed using a generally U-shaped rim 138. The rim 138 cooperates with the manifold gasket 74 to define the passageway 136. The passageway 136 communicates with the inlet passageway 92 and the inlet check valve 118. A cavity 140 is also formed in the lower surface 78 and is defined by a flange 142. The flange 142 has a low shoulder portion 144 that permits gas to flow from the cavity 140 to passageway 150. An internal filter 152 is held in the cavity 140 using a filter retainer 154. An O-ring 156 is also positioned in the cavity 140 to provide the necessary sealing so that the gas from the outlet check valve 120 passes through the internal filter 152. The filter 152 acts to remove particles or other contaminants that might pass from the outlet check valve 120 into the cavity 140.

In the case in which air is being supplied to a patient, who is unable to breathe on his own, the air enters the inlet passageway 92. From there, the air passes through the passageway 136. The pressure of the incoming air causes the leaf 122 of the inlet check valve 118 to be displaced outwardly and therby permit the air to pass from the passageway 136 into the space or cavity formed by the piston 10 and the walls of the cylinder 64. When the piston 10 is extended and moves towards the inner surface 110, the pressurized air moves the leaf 124 of the outlet check valve 120 so that the air passes therethrough into the cavity 140 having the filter 152. The air then passes by the low shoulder portion 144 into the passageway 150 and then to the outlet passageway 100 for delivery to the patient through the outlet stem 96.

In addition to being an efficient and effective unit for passing air during the patient's inspiration, the manifold 70 is also used or associated with other components to provide desired features. The inlet assembly 82 also includes a threaded portion 162 formed in the leg 88. A high-pressure relief valve assembly 164 is held in the threaded portion 162. The high-pressure relief valve assembly 164 includes a leaf 166 that is joined to a high-pressure relief valve 168. A spring 170 is positioned on the side of the high-pressure relief valve 168 opposite that of the leaf 166. The assembly 164 is held in the threaded hole 162 using a high-pressure relief fastener 172. The opening 162 communicates with a safety passageway 174, which leads to the passageway 150. The high-pressure relief valve assembly 164 is provided for safety reasons, i.e. to relieve unwanted high pressure that may develop because of a malfunction. Instead of undesired high pressurized gas being received by the patient to whom the apparatus of the present invention is connected, the high-pressure relief valve assembly 164 acts to vent the high-pressurized air to the atmosphere using the opening 162. The safety passageway 174 and the passageway 150 also provide an additional function. In the case in which the patient is able to breathe on his own, air delivered to the inlet assembly 82 is carried through the opening 162 and the passageway 174, 150, 100 to the patient because of the low pressure or vacuum created by the patient inspiring.

With regard to the outlet assembly 84, the exhalation stem 102 enables the metal piece of tubing 106 to be held therein for use in controlling an exhalation valve (not shown), which is located near the patient. The metal piece of tubing 106 communicates with a tube 176. Tube 176 extends to an electrical solenoid valve 178, which is held to the leg 94 of the outlet assembly 84 by a bracket member 180. Also connected to the solenoid 178 is a tube 182 which communicates with the tube 176 through the electrical solenoid valve 178, when it is energized. A hole is formed in the base member 86 of the manifold 70 for receiving a nipple 184. By this arrangement, a path for gas is provided from the passageway 160 of manifold 70 through the nipple 184 and tube 182 to the solenoid 178. When the patient is exhaling, the solenoid 178 is de-energized whereby the exhalation valve is opened to permit air exhaled by the patient to pass to the atmosphere. When the patient is inhaling, the solenoid 178 is energized to permit air to pass through the tube 182 to the tube 176 and the metal piece of tubing 106 to the exhalation valve whereby the valve is shut off.

In connection with the pressure stem 104 formed integral with the outlet assembly 94, the metal piece of tubing 108 that is held in a hole formed in the pressure stem 104 communicates with a pressure tube 190. The pressure tube 190 communicates with a pressure transducer (not shown) for use in sensing the patient's inspiration and expiration. This sensed information is used by the apparatus to provide air in accordance with the breathing cycle of the patient, in the case in which the patient is able to breathe on his own. This pressure information is also used to detect alarm conditions, such as patient disconnection or blockage.

Figure 8:
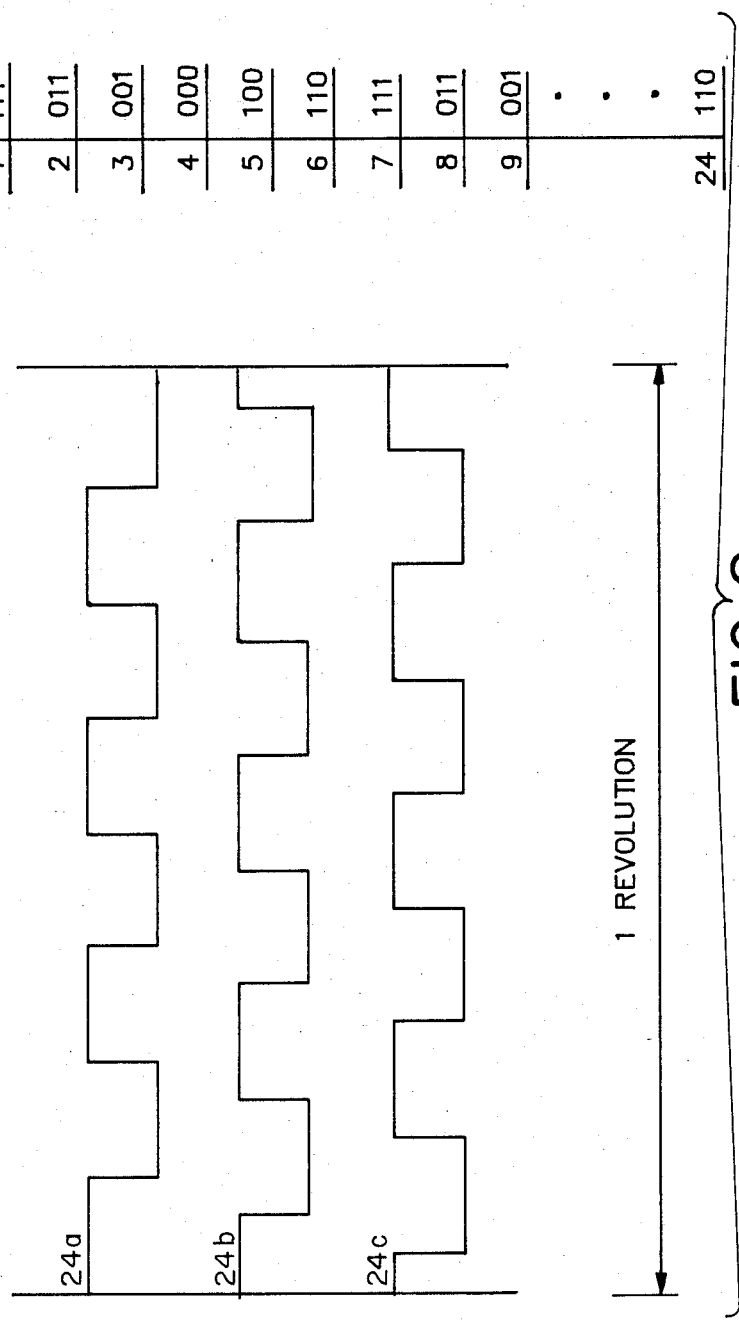
FIG. 8 is a pulsed waveform and bit pattern representative of the outputs from the three Hall sensors.

Returning back to FIGS. 1 and 2, the sensor assembly 24 includes a number of magnetic or Hall effect sensors 24a, 24b, 24c. Each of the three magnetic sensors 24a-24c is preferably held to the stator 22 of the motor 12. Each of the Hall sensors 24a-24c is spaced a relatively short distance from each other for sensing the rotation of the four permanent magnets contained in the rotor 20. The sensors 24a-24c are positioned so that the pulsed outputs therefrom, due to the sensing of the permanent magnet poles of the rotor 20 during rotation thereof, results in the pulsed outputs being out-of-phase relative to each other, as illustrated in FIG. 8. FIG. 8 represents a pulsed waveform for one revolution of the rotor 20. As can be seen, for each revolution of the rotor 20, a binary bit pattern having six different states repeats itself four times. Each of the states or codes is used in controlling the operation of the motor 12, as well as in determining the actual or current position of the piston 10 as it moves within the cylinder 64.

With regard to controlling the brushless-type DC electric motor 12, the outputs from the Hall sensors 24a-24c are sent to a ROM 204. The ROM 204 is programmed to provide a predetermined output, depending upon which of the six Hall sensor outputs are currently present. The output of the ROM 204 is applied to a motor driver circuit 206, which controls current to each of the motor windings 18a, 18b, and 18c, as depicted in FIG. 3. Each of the three motor coils 18a, 18b, 18c is driven by a pair of a number of driving transistors 210-210f of the power Darlington type. For example, motor coil 18b is driven by driving transistors 210d and 210e. In a preferred embodiment, the pairs of driving transistors 210a-210f of the motor driver circuit 206 are driven at about a 16 khz frequency. Because of this relatively rapid switching of the transistors, due to the applied 16 khz signal used in controlling the motor driver circuit 206, it is necessary to provide a current path for the current generated by the inductive coils 18a-18c, when they are not being energized by the associated pair of driving transistors 210a-210f. As such, the motor coils 18a–18c are used like inductors in a switching power supply. The motor driver circuit 206 also includes six diodes 212a–212f. A pair of the diodes, e.g. diodes 212d, 212e, provide a current path through capacitor 216 during the time the driving transistor pair 210d, 210e, for example, are off.

Ultimate control of the apparatus resides in a microprocessor 220. The microprocessor 220 communicates with a memory 222 that stores, among other things, a data table that is used in controlling the movement of the piston 10. The microprocessor 220 also provides information to the ROM 204 including the direction that the rotor 20 is to rotate, which depends upon the direction of desired piston 10 movement. The microprocessor 220 also informs the ROM 204 as to whether or not the exhalation solenoid is to be energized and whether the microprocessor 220 is functioning properly. A number of signal inputs are also sent to the microprocessor 220. A reference or magnetic sensor 224 sends information to the microprocessor 220 indicating whether the piston 10 is located at a reference position. Preferably, the reference sensor 224 is located near the gear box assembly 14 and the crank arm assembly 16 in order to sense when the piston 10 is positioned at a known location near the bottom end of its stroke, i.e. when the piston 10 is near its greatest extended position adjacent to the base member 86. The microprocessor 220 relies on this information from the reference sensor 224 to determine piston position for use in controlling motor operation, as will be subsequently described. An operator panel 226 communicates with the microprocessor 220 and includes input switches or dials used in selecting a number of desired functions or parameters, including the volume of air to be delivered to a patient, who is unable to breathe on his own.

In connection with monitoring and controlling the volume defined by the piston 10 and the inner surface 110 of the base member 86 and the walls of the cylinder 64 between the piston 10 and the inner surface 110, the microprocessor 220 monitors movement of the piston 10 by counting pulses using the outputs of the magnetic sensors 24a–24c.

In the present invention, a table has been formulated that correlates information relating to Hall pulses counted and a volume or a position of the piston. The contents of the table were determined taking into account the non-linearity that exists because of the crank arm hardware used in the invention. For example, the number of pulses counted to achieve a 200 cc piston displacement from a reference position is not twice the number of pulses counted to achieve a 100 cc displacement from the same reference position. This lack of proportionality is due to the fact that the crank arm 50 exhibits sinusoidal motion during movement of the piston 10 and there is different displacement or movement of the piston 10 for each revolution of the rotor 20, depending upon the current position of the piston 10 and crank arm 50. These factors have been taken into consideration in developing the table stored in memory for correlating volume or piston position and the number of pulses counted, which are outputted by the Hall sensors 24a–24c. After the corresponding number of pulses have been counted for the desired volume, retraction motion of the piston 10 is stopped.

Software that is utilized by the microprocessor 220 in monitoring and controlling the position of the piston 10, including the formulated table, is provided in the Microfiche Appendix, which forms a part of this application.

As represented in FIG. 1, the apparatus also includes circuitry for controlling the rate of movement or velocity of the brushless-type DC electric motor 12. Comparator circuitry 230 receives an input signal proportional to the speed derived from settings selected by the operator. The rate of piston movement is intended to provide desired inspiration and expiration times for the patient. The speed-related signal is received by a speed/volume switch 232 and, during normal operation, the speed-related signal is outputted from the switch 232 and applied to the comparator circuitry 230. Also inputted to the comparator circuitry 230 is a voltage signal, which is proportional to the actual frequency or speed of the DC motor 12. This voltage signal is outputted by a frequency-to-voltage converter 234, which receives its input from the ROM 204. The signal to the frequency-to-voltage converter 234 from the ROM 204 represents the actual speed of the motor. The comparator circuitry 230 compares the selected speed provided through the speed/volume switch 232 with the voltage signal from the frequency-to-voltage converter 234. In cases in which there is a difference, the comparator circuitry 230 outputs a signal to the ROM 204 for controlling the application of power to the motor 12.

To enhance the safety of the apparatus, it includes a back-up timer 238, which is responsive to the reference sensor 224 and communicates with the ROM 204. In the case of a malfunction with the microprocessor 220, for example, motor control is achieved using the ROM 204, the reference sensor 224, and the back-up timer 238. In particular, the speed/volume switch 232 switches state whereby a signal relating to the volume selected by the operator is applied to the comparator circuitry 230, instead of the speed-related signal. The reference sensor 224 detects that the piston 10 is located near bottom dead center and, upon detection, controls the activation of the back-up timer 238, which causes the piston to retract. In one embodiment, the back-up timer 238 is set for two seconds. At the completion of the two seconds, the back-up timer 238 outputs a signal to the ROM 204, which causes the motor to reverse and the piston 10 to once again begin its downstroke whereby it is extended towards the base member 86. As during normal operation, the ROM 204 sends a signal relating to motor speed to the frequency-to-voltage converter 234. The output of the converter 234 is compared with the volume-related signal, which has been modified by a known factor so that the signal relating to the selected volume can be properly compared with a voltage signal proportional to the speed of the motor 12. Until a correspondence is reached, the comparator circuitry 230 adjusts the speed of the motor 12. As can be appreciated, the pre-established time of the back-up timer 238 acts as a substitute for the microprocessor's counting of Hall sensor pulses.

In operating the ventilator of the present invention with a patient who is unable to breathe on his own, the operator or user selects a desired volume of air or other gas to be delivered to the patient using the operator panel 226. The operator also selects a speed or rate at which the piston 10 is to deliver the gas. The signal relating to the speed is calculated by the microprocessor and applied to the switch 232 and outputted to the comparator circuitry 230. At the same time the ROM 204 is outputting a signal relating to the actual speed of the motor 12 using the information supplied by the outputs of the three Hall sensors 24a–24c. The signal from the ROM 204 that is converted to a voltage signal representative of actual motor speed by the frequency-to-voltage converter 234 so that a voltage signal representative of the actual speed is applied to the comparator circuitry 234. The comparator circuitry 234 determines whether there is a difference between the selected speed and the actual speed and provides an output signal to the ROM 204 for use in controlling the turning on and off of the motor 12, depending upon the magnitude and polarity of any difference.

Also simultaneously with the activation of the motor 12 and the movement of the piston 10, the three Hall sensors 24a–24c output out-of-phase pulses to the microprocessor 220. During the portion of the piston stroke when the piston 10 is being retracted from the reference position, the Hall pulses are being counted by the microprocessor 220 from the time the piston began its retraction from bottom dead center. The microprocessor 220 compares the number of counted Hall pulses with a predetermined count. The predetermined count corresponds to a desired volume selected by the operator using the operator panel 226. During the time that the piston 10 is retracting to reach the desired volume, the microprocessor 220 continues to compare the current count of Hall pulses with the predetermined count, which is based on the selected volume. When the actual count equals the selected count, the microprocessor controls the turning off of the motor 12 so that the piston 10 is in its desired position. From this selected, retracted position, the piston 10 can be extended to cause the air received through the inlet check valve 118 to be pressurized through the outlet check valve 120 for passing to the patient using the outlet passageway 100 and the outlet stem 96. In obtaining the predetermined count of Hall pulses that corresponds to the selected volume or piston position, the microprocessor 220 accesses the table in the memory 222 in order to correlate the selected volume with a corresponding number of pulses. Greater resolution is accomplished by extrapolating between succeeding values stored in the table.

The movement of the piston 10 is achieved through the rotation of the rotor 20 as the pulses from the sensor assembly 24 are decoded by the ROM 204 to control the operation of the driving transistors 210a–210f for use in energizing the motor coils 18a–18c. The rotation of the rotor 20 causes the crank arm assembly 16 to move in one direction, with the rotation of the rotor 20 being coupled to the crank arm assembly 16 by the gear box assembly 14 so that a high resolution of rotor rotation to movement of the crank arm 50 is achieved. Such high resolution enables the apparatus to finely control incremental movements of the piston 10 in order to achieve a desired volume. After the piston 10 reaches the desired retracted position and thereby defines the selected volume, the micrprocessor 220 controls the change in direction of the piston 10 by providing an input to the ROM for use in controlling the energization of the motor coils 18a–18c so that the rotor reverses its rotational direction and thereby causes the crank arm 50 to move in the opposite direction. Because of this capability, the crank arm 50 is able to move like a pendulum, and a complete rotation of the crank arm 50 is not required for proper piston extension and retraction.

Based on the foregoing detailed description of the present invention, a number of salient features of the disclosed apparatus are readily recognized. The microprocessor under software control, together with the brushless-type DC electric motor, enable the ventilator of the present invention to significantly reduce the number of mechanical components that have been utilized in previous ventilators. The brushless-type motor also eliminates any need to replace brushes in contrast to the brush-type motors that are found in prior art ventilators. The microprocessor control and the brushless-type DC motor also enable the crank arm to move in a pendulum-like fashion whereby movement and wear of mechanical components are reduced. Additionally, the control provided in the present invention provides a relatively more rapid adjustment of volume than was found in previous ventilators.

Although the present invention has been described with reference to a particular embodiment, it should be appreciated that variations and modifications can be effected within the spirit and scope of this invention.

What is claimed is:

1. A lung ventilating system, comprising:

motor means including a brushless-type electric motor having a number of coils;

housing means;

piston means movable relative to said housing means;

linkage means operatively connecting said motor means and said piston means;

first means for sensing movement of said motor means, wherein the position of said piston means relative to said housing means is continuously determinable during movement of said piston means using said motor means sensed movement;

second means communicating with said first means for controlling the operation of said motor means and thereby the movement of said piston means, said second means including processing means communicating with said first means, said processing means processing information received from said first means for controlling direction of movement of said piston means and for controlling activation of said motor means;

programmed memory means communicating with said first means and said processing means for providing a predetermined output for controlling the energization of said coils of said motor means, said programmed memory means also outputting a velocity-related signal relating to the speed of said motor means;

reference sensor means operatively associated with said piston means for sensing a reference position of said piston means relative to said housing means and communicating said reference position to said processing means;

speed controlling means communicating with said programmed memory means and receiving said velocity-related signal, said speed controlling means also continuously inputting a desired velocity-related signal to said programmed memory means relating to a desired speed of said motor means, said desired velocity-related signal being continuously adjusted, the amount of adjustment depending upon the magnitude of difference between said received velocity-related signal and a predetermined magnitude, said predetermined output of said programmed memory means depending on said input from said first means, said input from said processing means, and said input from said speed controlling means; and input means communicating with at least one of said processing means and said speed controlling means for use in controlling the speed and amount of movement of said piston means.

2. A lung ventilating system, comprising:
motor means having shaft means;
housing means;
piston means movable relative to said housing means;
connecting rod means having a first portion and a second portion, said second portion being connected to said piston means;
a fixed radius crank arm being rotatable relative to said shaft means of said motor means and having a first portion and a second portion, said first portion being connected to said shaft means to define a first connection position, said second portion being connected to said first portion of said connecting rod means to define a second connection position, wherein a distance is defined between said first connection position and said second connection position, said distance remaining substantially the same during operation of the lung ventilating system;
first means for sensing movement of said motor means, wherein the position of said piston means relative to said housing means is continuously determinable during movement of said piston means using said motor means sensed movement;
second means communicating with said first means for controlling the operation of said motor means and thereby movement of said piston means; and
reference means operatively associated with at least one of said piston means and said motor means for inputting to said second means a reference position relating to a position of said piston means, wherein said reference means, said fixed radius crank arm, and said first and second means cooperate to cause desired reciprocating movement of said piston means in which said fixed radius crank arm is able to rotate less than 360° for desired positioning of said piston means relative to said housing means.

3. A system, as claimed in claim 1, wherein:
said linkage means includes gear means operatively engaging said motor means for use in providing a higher resolution to improve the controlling of the position of said piston.

4. A system, as claimed in claim 1, wherein: said motor means includes a rotor that is movable in both clockwise and counter-clockwise directions under the control of said second means.

5. A system, as claimed in claim 1, wherein:
said first means includes at least three magnetic sensors spatially disposed relative to each other adjacent to said motor means wherein each of the outputs of said three magnetic sensors communicates with said second means and is out-of-phase with the other two of said magnetic sensors.

6. A system, as claimed in claim 5, wherein:
said motor means includes a stator and a rotor and each of said magnetic sensors is fastened to said stator adjacent to said rotor.

7. A system, as claimed in claim 1, wherein:
said reference sensor means is operatively connected to said housing means adjacent to one end of said housing means.

8. A system, as claimed in claim 1, wherein:
said processing means includes means for counting pulses received from said first means and means for comparing said counted number of pulses with a predetermined number, said means for comparing operatively communicating with said programmed memory means.

9. A system, as claimed in claim 1, wherein:
said processing means includes means communicating with said first means for storing data relating to a correlation between a number of pulses and a selected volume defined by said piston means and said housing means, said number of pulses being predetermined and depending upon the position of said piston means relative to said housing means.

10. An apparatus, as claimed in claim 9, wherein:
said means for storing data stores a plurality of numbers, each of which is correlated with a value relating to piston position, and wherein a non-linear relationship exists between said correlated data.

11. An apparatus, as claimed in claim 1, wherein said housing means includes:
a cylinder; and
a one-piece manifold to which said cylinder is sealingly mounted, said manifold including a number of passageways formed in a side of said manifold opposite from the side thereof to which said cylinder is mounted, said passageways for carrying gas to a patient.

* * * * *